United States Patent

Huth et al.

Patent Number: 5,543,519
Date of Patent: Aug. 6, 1996

[54] 3-ARYL OR 3-HETARYL-β-CARBOLINES, THEIR PRODUCTION AND USE IN PHARMACEUTICAL AGENTS

[75] Inventors: Andreas Huth; Dieter Seidelmann; Ralph Schmiechen; Herbert Schneider; Lechoslaw Turski, all of Berlin, Germany

[73] Assignee: Schering Aktiengesellschaft, Berlin, Germany

[21] Appl. No.: 329,051

[22] Filed: Oct. 25, 1994

Related U.S. Application Data

[63] Continuation of Ser. No. 39,127, Apr. 15, 1993, abandoned.

[30] Foreign Application Priority Data

Jun. 15, 1991 [DE] Germany ............ 41 20 109.4

[51] Int. Cl.⁶ ............ C07D 471/04; C07D 401/12; C07D 405/12; C07D 409/12
[52] U.S. Cl. ............ 544/238; 544/333; 546/86; 546/87
[58] Field of Search ............ 546/85, 86, 87; 514/292; 544/238, 333

[56] References Cited

U.S. PATENT DOCUMENTS

| | | | |
|---|---|---|---|
| 4,435,403 | 3/1984 | Braestrup et al. | 514/292 |
| 4,596,808 | 6/1986 | Braestrup et al. | 514/292 |
| 4,645,773 | 2/1987 | Engelstoft et al. | 514/292 |
| 4,705,856 | 11/1987 | Biere | 546/21 |
| 4,877,792 | 10/1989 | Biere et al. | 514/292 |
| 4,894,377 | 1/1990 | Seidelmann et al. | 514/292 |
| 4,933,345 | 6/1990 | Huth et al. | 514/253 |
| 4,945,090 | 7/1990 | Schmiechen et al. | 514/232.8 |

OTHER PUBLICATIONS

Liebigs Annalen Der Chemie, vol. 86, No. 10 (Oct. 1986), Weinheim DE, pp. 1749–1764; H. Biere et al.: "Eine neue und besonders einfache Synthese von Zentralaktiven beta–Carbolin–derivaten", see p. 1749, paragraph 1, see p. 1762; Example 6K.

*Primary Examiner*—Alan L. Rotman
*Attorney, Agent, or Firm*—Millen, White, Zelano, & Branigan, P.C.

[57] ABSTRACT

Compounds of formula I are described

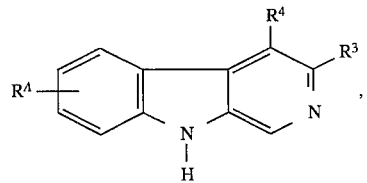

in which
$R^3$ represents a $C_{6-12}$-aryl or hetaryl radical, optionally substituted singly or multiply with $C_{1-4}$-alkyl, $C_{3-7}$-cycloalkyl, halogen, $C_{1-4}$-alkoxy-$C_{1-2}$-alkyl, phenyl or amino, the process for their production and their use in pharmaceutical agents.

4 Claims, No Drawings

3-ARYL OR 3-HETARYL-β-CARBOLINES, THEIR PRODUCTION AND USE IN PHARMACEUTICAL AGENTS

This application is a continuation of application Ser. No. 08/039,127, filed Apr. 15, 1993, abandoned.

The invention relates to new 3-hetaryl or 3-aryl-β-carbolines, their production and use in pharmaceutical agents.

From numerous publications, such as, for example, from EP-A-110814, it is known that β-carbolines affect the central nervous system and are suitable as psychopharmaceutical agents. It was shown in a surprising way that the β-carbolines substituted according to the invention in 3-position are bioavailable over a prolonged period and at the same time have a good affinity for the benzodiazepine receptors.

The compounds according to the invention have formula I

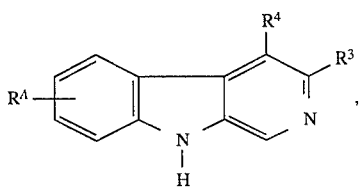

in which $R^A$ means halogen, $-CHR^1-R^2$, phenyl optionally substituted with halogen, $C_{1-4}$-alkoxy or amino, hetaryl or $OR^5$ and can be single to double and $R^1$ represents hydrogen or $C_{1-4}$-alkyl, $R^2$ represents hydrogen, $C_{1-4}$-alkyl, $-O-C_{1-4}$-alkyl or an optionally substituted phenyl, benzyl or phenoxy radical and $R^5$ represents hydrogen, $C_{1-6}$-alkyl, $C_{3-7}$-cycloalkyl or an optionally substituted phenyl, benzyl, hetaryl or benzocondensed hetaryl radical, $R^4$ represents hydrogen, $C_{1-4}$-alkyl or $C_{1-4}$-alkoxy-$C_{1-2}$-alkyl and $R^3$ represents a $C_{6-12}$-aryl or hetaryl radical optionally substituted singly or multiply with $C_{1-4}$-alkyl, $C_{3-7}$-cycloalkyl, halogen, $C_{1-4}$-alkoxy-$C_{1-2}$-alkyl, phenyl or amino as well as their isomers and acid addition salts.

Substituent $R^A$ can be in the A ring in 5–8 position, preferably in 5, 6 or 7 position.

An alkyl contains respectively straight-chain as well as branched-chain radicals such as, for example, methyl, ethyl, propyl, isopropyl, butyl, isobutyl, sec. butyl, tert. butyl, pentyl, isopentyl and hexyl.

By halogen is meant fluorine, chlorine, bromine and iodine respectively.

Cycloalkyl respectively can stand for cyclopropyl, cyclobutyl, cyclopentyl, cyclohexyl, cycloheptyl and 2-methylcyclopropyl, and 3–5 carbon atoms are preferred.

If $R^5$ or $R^A$ means a hetaryl radical, then the latter is 5- or 6-membered and contains 1–3 heteroatoms such as nitrogen, oxygen and/or sulfur. For example, the following 5- and 6-ring heteroaromatic compounds can be mentioned: pyridine, pyrimidine, pyrazine, pyridazine, furan, thiophene, pyrrole, thiazole, imidazole, triazine.

Pyridine, thiophene and furan are to be considered as the preferred hetaryl radical $R^A$.

If $R^5$ is a benzocondensed hetaryl radical, then it preferably contains 1–2 nitrogen atoms such as quinoline, isoquinoline, quinoxaline or benzimidazole.

The substituent of phenyl, benzyl, hetaryl and benzocondensed hetaryl radical $R^5$ can be single to triple in any position. Suitable substituents are halogens, nitro, cyano, $C_{1-4}$-alkyl, $C_{1-4}$-alkoxy, amino, $C_{1-4}$-alkoxycarbonyl, $C_{1-4}$-alkylthio and trifluoromethyl, and for the phenyl and benzyl radical, the single to double substitution with halogens is preferred.

As preferred hetaryl radicals and benzocondensed hetaryl radicals $R^5$ nitrogen-containing heterocycles are to be considered, that optionally are single to double substituted with halogen, $C_{1-4}$-alkyl, $C_{1-4}$-alkoxy or trifluoromethyl, especially with halogen.

As substituents of phenyl, benzyl and phenoxy radical $R^2$ the substituents of the aromatic compounds mentioned for $R^5$ are suitable, especially halogen such as chlorine and bromine.

Aryl and hetaryl radical $R^3$ can be present as monocyclic or bicyclic compounds and contain 5–12 ring atoms, preferably 5–9 ring atoms, such as, for example, phenyl, biphenylyl, naphthyl, indenyl as aryl radical and thienyl, furyl, pyranyl, pyrrolyl, pyrazolyl, pyridyl, pyrimidinyl, pyridazinyl, oxazolyl, isooxazolyl, thiazolyl, isothiazolyl, 1,3,4-oxadiazol-2-yl, quinolyl, isoquinolyl, benzo[1]thi-enyl, benzofuryl as hetaryl radical with 1–3 heteroatoms such as sulfur, oxygen and/or nitrogen.

The substituent of aryl and hetaryl radical $R^3$ can be single or triple, especially single.

As preferred embodiments there can be mentioned: $R^A$ in the meaning of $OR^5$, and $R^5$ means $C_{1-6}$-alkyl or an optionally single or double substituted phenyl or benzyl radical or a five or six membered optionally benzocondensed heterocyclic compound with 1–3 nitrogen atoms, that is optionally single to double substituted, and $R^3$ meaning phenyl optionally substituted with halogen or $C_{1-4}$-alkoxy or an optionally substituted five or six membered heterocyclic compound with 1–3 heteroatoms, such as 1,3,4-oxadiazol-2-yl, thienyl, pyrrolyl, pyridyl, thiazolyl, oxazolyl or a benzocondensed heterocyclic compound such as benzothienyl. As substituents of the thiazolyl radical, $C_{1-4}$-alkyl and phenyl are to be considered as preferred and as substituent of the 1,3,4-oxadiazolyl radical, $C_{1-4}$-alkyl, $C_{1-4}$-alkoxy-$C_{1-2}$-alkyl, $C_{3-7}$cyclopropyl and amino are preferred.

If a chiral center is present the compounds of formula I in the form of stereoisomers and their mixtures can be present.

The physiologically compatible acid addition salts are derived from the known inorganic and organic acids such as, for example, hydrochloric acid, hydrobromic acid, sulfuric acid, phosphoric acid, formic acid, acetic acid, benzoic acid, maleic acid, fumaric acid, succinic acid, tartaric acid, citric acid, oxalic acid, glyoxylic acid as well as from alkanesulfonic acids and arylsulfonic acids, such as, for example, methanesulfonic acid, ethanesulfonic acid, benzenesulfonic acid, p-toluenesulfonic acid, i.a.

The compounds of formula I as well as their acid addition salts are usable as pharmaceutical agents because of their affinity to benzodiazepine receptors and have an antagonistic, inverse agonistic and agonistic effect on the properties known of the benzodiazepines. At the same time the compounds according to the invention show an extended duration of action and are distinguished by anxiolytic effectiveness. The affinity to the benzodiazepine receptors is determined by tests of the displacement capacity of radioactively labeled flunitrazepam by the benzodiazepine receptors. For examination of the anxiolytic effect the compounds are tested in a 4-plate test according to the methods of Boissier et al, Eur. J. Pharmacol. 4, 145–150 (1968). Thus the minimal effective dosage (MED) is given, that increases the locomotor activity of the afflicted mice after i.p. treatment. A reduction of the activity in the 4-plate test without being afflicted indicates a sedative effect.

The compounds of formula I are suitable especially for the treatment of anxiety accompanied by depression and disturbed sleep.

For use of the compounds according to the invention as pharmaceutical agents they are put in the form of a pharmaceutical preparation, that, besides the active ingredient for enteral or parenteral administration, contains suitable pharmaceutical, organic or inorganic inert vehicles such as, for example, water, gelatin, gum arabic, lactose, starch, magnesium stearate, talc, vegetable oils, polyalkyleneglycols, etc.

The pharmaceutical preparations can be available in solid form, for example, as tablets, coated tablets, suppositories, capsules or in liquid form, for example, as solutions, suspensions or emulsions. Moreover, optionally, they contain auxiliary agents such as preservatives, stabilizers, wetting agents or emulsifiers, salts for changing the osmotic pressure or buffers.

Especially suitable for parenteral use are injection solutions or suspensions, especially aqueous solutions of the active compounds in polyhydroxy-ethoxylated caster oil.

As vehicle systems surface-active auxiliary agents such as salts of bile acids or animal or vegetable phospholipids, but also their mixtures as well as liposomes or their components can be used.

Especially suitable for oral use are tablets, coated tablets or capsules with talc and/or hydrocarbon vehicles or binders, such as, for example, lactose, corn or potato starch. The use can even take place in liquid form, such as, for example, as juice to which a sweetener is optionally added.

The compounds according to the invention are generally introduced in a dose unit of 0.05 to 100 mg of active substance in a physiologically compatible vehicle.

The compounds according to the invention generally are used in a dose of 0.1 to 300 mg/day, preferably 0.1 to 30 mg/day, especially preferred 1–20 mg/day, for example as anxiolytic agents analogous to diazepam.

The production of the compounds according to the invention takes place according to methods known in the art. For example, compounds of formula I are achieved in that a) a compound of formula II

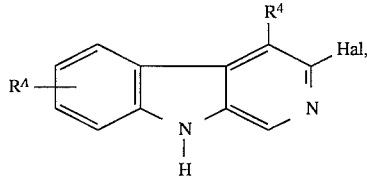

in which $R^A$ and $R^4$ have the above meaning and Hal is halogen, is arylated in the presence of a nickel or palladium catalyst with an organometallic compound of formula III

   III, in which $R^3$ has the above meaning,

Me means a metal atom,

X means halogen, hydroxy or $C_{1-4}$-alkyl and n means 1 to 3, or b) a compound of formula IV

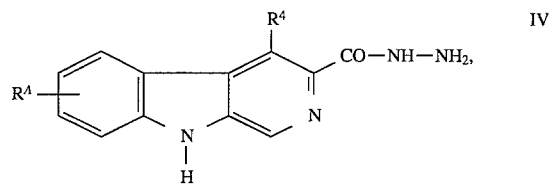

in which $R^A$ and $R^4$ have the above meaning, is cyclized with orthocarboxylic acid esters to compounds of formula I with $R^3$ meaning a 1,3,4-oxadiazol-2-yl radical, that is optionally substituted with $C_{1-4}$-alkyl, $C_{1-4}$-alkoxy-$C_{1-2}$-alkyl, phenyl or $C_{3-7}$-cycloalkyl or is cyclized with bromocyanogen to a compound of formula I with $R^3$ meaning a 5-amino-1,3,4-oxadiazol-2-yl radical or c) a compound of formula V

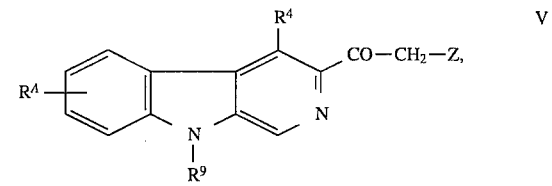

in which $R^A$ and $R^4$ have the above meaning, Z is halogen and $R^9$ represents hydrogen or a protective group, is cyclized with thiocarboxylic acid amides to compounds of formula I with $R^3$ meaning a thiazol-4-yl radical optionally substituted in 2-position and then the protective group is optionally cleaved off or d) a compound of formula VI

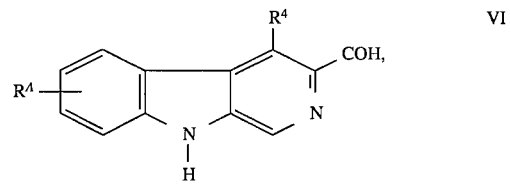

in which $R^A$ and $R^4$ have the above meaning is cyclized with tosylmethylisocyanide in the presence of a base to compounds of formula I with $R^3$ meaning an oxazol-5-yl radical and optionally then the benzyl group $R^5$ is cleaved off or $R^A$ meaning hydroxy is etherified or the isomers separated or the acid addition salts formed.

The arylation according to process variant a) takes place in a solution or in a suspension in inert solvents at temperatures of 0° C. up to the boiling temperature of the reaction mixture.

As solvents, for example, cyclic and acyclic ethers such as diethyl ether, tetrahydrofuran and dioxane, hydrocarbons such as toluene and benzene as well as aprotic, polar solvents such as dimethylformamide, dimethylacetamide, N-methylpyrrolidone, i.a., are suitable. In the case of boron an addition of protic solvents such as, e.g., alcohol, is not harmful.

As halogen hal, especially bromine and iodine are to be considered.

The organometallic compound of general formula III contains as metal atom lithium, magnesium, zinc, tin or boron, and substituent X, depending on the valence of the metal atom, can be single to triple, and X as halogen is especially chlorine or bromine.

Suitable nickel and palladium catalysts are, for example, 1,3-diphenylphosphinopropane-nickel-II-chloride, bis-tri-o- tolylphosphine-palladium-II-chloride, bis-triphenylphosphine-palladium-II-chloride, tetrakis-triphenylphosphine-palladium-(O) and 1,1'-bis-diphenylphosphinoferrocenepalladium-II-chloride.

The representation of 1,3,4-oxadiazoles according to process variant b) takes place by heating of β-carboline-3-carboxylic acid hydrazdes with orthocarboxylic acid esters in solution or in suspension and then cyclization in the presence of a base such as, for example, alkali alcoholates such as sodium or potassium ethylate, -tert. butylate.

As solvents the corresponding alcohols are suitable.

The reaction takes place at temperatures up to the boiling temperature of the reaction mixture and is completed after approximately 2–10 hours.

5-Amino-1,3,4-oxadiazoles are produced according to process variant b) by cyclization of the compounds of formula IV with bromocyanogen in protic solvents such as, for example, alcohols at elevated temperature, preferably 20°–50° C., and then treated with a base such as, for example, ammonia.

For the introduction of the thiazole group according to process variant c) compounds of formula V, especially 3-bromoacetyl or 3-chloroacetyl-β-carbolines with thiocarboxylic acid amides such as thioformamide, $C_{1-4}$-alkyl-CSNH$_2$, thiobenzoic acid amide in protic solvents such as alcoholates, are refluxed.

Optionally present protective groups in 9-position of the β-carboline such as, for example, alkanoyl, arylsulfonyl, alkylsulfonyl or trialkylsilyl protective groups can be cleaved off with the usual methods such as treatment with a base, for example alkali alcoholate or hydroxide or acids such as dilute mineral acid or with fluorides such as cesium fluoride at room temperature or elevated temperature.

For the production of oxazoles according to process variant d) 3-carbaldehyde-β-carbolines of formula VI are reacted with tosylmethyl isocyanide in suspension or in solution. The reaction takes place in the presence of a base such as alkalicarbonates or alkali alcoholates in protic solvents such as alcohols at temperatures up to the boiling temperature of the reaction mixture and is completed after about 1–3 hours.

If cleaving off of radical $R^5$ is desired, then it takes place according to the processes described in EP-A-130 140 or by hydrogenolytic cleavage.

The optionally following etherification of the free hydroxy group takes place according to the process described in EP-A-237 467, by reactive compound $R^A$-Y in which Y means, for example, halogen, tosylate, mesylate or triflate, being reacted in the presence of a base such as alkali alcoholate or hydroxide in polar solvents such as dimethylsulfoxide, dimethylformamide, acetonitrile or alcohols at room temperature or elevated temperature, optionally in the presence of phase transfer catalysts.

The isomer mixtures can be separated according to the usual methods, such as, for example, crystallization, chromatography or salt formation, in the diastereomers or enantiomers.

For the formation of the physiologically compatible acid addition salts a compound of formula I, for example, is dissolved in a little alcohol and mixed with a concentrated solution of the desired acid.

If the production of the initial compounds is not described, they are known or are producible analogously to known compounds or processes described here.

3-Halogen-β-carboline derivatives of formula II are obtained according to the methods described in EP-A-110 814 or according to a Sandmeyer variant in bromoform as solvent with isoamylnitrite in the presence of polyethylene glycol.

The representation of the compounds of formula IV takes place by heating of β-carboline-3-carboxylic acid alkyl ester with hydrazine hydrate.

By oxidation of 3-hydroxymethyl-β-carbolines according to the process described in EP-A-54 507 or according to the syntheses described in EP-A-305 322, 3-carbaldehyde-β-carbolines of formula VI are obtained.

The following examples are to explain the process according to the invention.

Production of the initial materials:

A.) 6-Benzyloxy-4-methoxymethyl-β-carboline-3-carboxylic acid is produced according to the process given in EP-A-161 574 from 6-benzyloxy-4-methoxymethyl-β-carboline-3-carboxylic acid isopropyl ester.

Melting point 243° C.

B.) 3-Trimethylsilylethyloxycarbonylamino-6-benzyloxy-4-methoxymethyl-β-carboline 3.62 g of 6-benzyloxy-4-methoxymethyl-β-carboline-3-carboxylic acid is dissolved clear in 50 ml of dimethylformamide, mixed with 4.3 g of phosphoric acid diphenylesterazide and 1.4 ml of triethylamine and stirred for 2 hours at 80° C. bath temperature under argon. After cooling it is mixed with 2.9 ml of 2-trimethylsilylethanol and heated for 4 hours to 80° C. bath temperature. After standing overnight it is concentrated by evaporation in a vacuum. The residue is taken up in ethyl acetate and washed once each with saturated sodium bicarbonate solution and common salt solution. The organic phase is dried, filtered, and concentrated by evaporation. The residue is introduced without further purification in the next step.

C.) 3-Amino-6-benzyloxy-4-methoxymethyl-β-carboline 5 g of 3-trimethylsilylethoxycarbonylamino-6-benzyloxy-4-methoxymethyl-β-carboline in 40 ml of tetrahydrofuran is heated with 22 ml of tetrabutylammonium fluoride for 3 hours to 50° C. After distilling off the solvent it is taken up in ethyl acetate and washed once each with a saturated sodium-carbonate and saturated common salt solution. The organic phase is dried, filtered and concentrated by evaporation. The residue is chromatographed on silica gel with methylene chloride: ethanol=10:2 as eluant. After concentration by evaporation of the corresponding fractions and absorptive precipitation with cyclohexane/ethyl acetate, 1.32 g of 3-amino-6-benzyloxy-4-methoxymethyl-β-carboline is obtained.

D.) 3-Bromo-6-benzyloxy-4-methoxymethyl-β-carboline 1 g of 3-amino-6-benzyloxy-4-methoxymethyl-β-carboline in 32 ml of bromoform is mixed with 0.6 ml of HBr/glacial acetic acid (33%) and 5 g of PGE$^{200}$. 0.46 ml of isoamylnitrite is added at 9° C. and it is maintained for 30 minutes at this temperature. Then 0.56 g of copper(I) bromide is added to this batch. After heating of the batch to room temperature it is diluted with methylene chloride within one hour and extracted once each with dilute ammonia solution and with water. The organic phase is dried, filtered and concentrated by evaporation. The residue is chromatographed on silica gel with methylene chloride: ethanol=15:1. The corresponding combined fractions are concentrated by evaporation and absorptively precipitated with ethyl acetate/hexane. 0.54 g of 3-bromo-6-benzyloxy-4-methoxymethyl-β-carboline is obtained.

E.) 6-Benzyloxy-4-methoxymethyl-3-acetyl-9-tosyl-β-carboline 8.4 g of 6-benzyloxy-4-methoxymethyl-9-tosyl-β-carboline-3-carboxylic acid isopropyl ester is dissolved in 500 ml absolute tetrahydrofuran and cooled to −60° C. 15 ml of a 1.5 molar ethereal methyllithium solution is added drop by drop to this solution under argon atmosphere and then stirred for another 4 hours at −60° C. After heating to room temperature the reaction solution is mixed with saturated ammonium chloride solution, extracted with methylene chloride, dried and concentrated by evaporation. The resulting crude product is chromatographed on silica gel with cyclohexane: ethyl acetate=8:2. 4.1 g of 6-benzyloxy-4-methoxymethyl-3-acetyl-9-tosyl-β-carboline with a melting point of 173–175° C. is obtained.

F.) Bromination 2.29 g of 6-benzyloxy-4-methoxymethyl-3-acetyl-9-tosyl-β-carboline is stirred with the double molar amount of phenyltrimethylammonium tribromide in 100 ml of absolute tetrahydrofuran for 4 days at room temperature. The reaction mixture is evaporated to dryness, taken up in methylene chloride, washed with saturated NaCl solution, dried on Sikkon and concentrated by evaporation. The crude product is chromatographed on silica gel (cyclohexane/ethyl acetate=8+2). 1.9 g of 6-benzyloxy-3-bromoacetyl-4-methoxymethyl-9-tosyl-β-carboline is obtained. Melting point 165° C. (decomposition).

G.) 5-Benzyloxy-4-methoxymethyl-β-carboline-3-carboxylic acid-hydrazide 1.56 g of 5-benzyloxy-4-methoxymethyl-β-carboline-3-carboxylic acid-ethyl ester is refluxed in 20 ml of hydrazine hydrate (80%) for 4 hours. After cooling, the precipitated crystals are suctioned off and dried. 1.2 g of 5-benzyloxy-4-methoxymethyl-β-carboline- 3-carboxylic acid-hydrazide of a melting point of 212°–213° C. is obtained.

In a analogous way, there are produced:

6-benzyloxy-4-methoxymethyl-β-carboline-3-carboxylic acid-hydrazide, melting point 228°–231° C.

5-(4-fluorobenzyloxy)-4-methoxymethyl-β-carboline-3-carboxylic acid-hydrazide, melting point 218°–225° C.

5-(4-chlorophenoxy)-4-methoxymethyl-β-carboline-3-carboxylic acid-hydrazide, melting point 194°–198° C.

5-isopropoxy-4-methyl-β-carboline-3-carboxylic acid hydrazide, melting point 240°–243° C.

6,7-dimethoxy-4-ethyl-β-carboline-3-carboxylic acid hydrazide, melting point 253–255° C.

6-benzyloxy-4-ethyl-β-carboline-3-carboxylic acid hydrazide, melting point 265°–268° C.

EXAMPLE 1

6-Benzyloxy-3-phenyl-4-methoxymethyl-β-carboline 476 mg of 3-bromo-6-benzyloxy-4-methoxymethyl-β-carboline is introduced in 10 ml of toluene and 5 ml of ethanol, mixed with 41 mg of tetrakis(triphenylphosphine)-palladium(0) and stirred for 5 minutes. Then 177 mg of phenylboronic acid and 1.5 ml of a 2 m- soda solution are added and then heated for 3 hours to 95° C. After concentration by evaporation it is taken up in a lot of ethyl acetate and washed once each with water and saturated common salt solution. After drying, filtration and concentration by evaporation, it is recrystallized. 372 mg of 6-benzyloxy-3-phenyl-4-methoxymethyl-β-carboline of a melting point of 205°–206° C. (ethanol, methylene chloride, hexane) is obtained.

In a analogous way, there are produced:

5-benzyloxy-4-methoxymethyl-3-(2-thienyl)-β-carboline, melting point 189°–191° C.

5-benzyloxy-4-methoxymethyl-3-(2-pyrrolyl)-β-carboline, melting point 203°–205° C.

6-benzyloxy-4-methoxymethyl-3-(2-thienyl)-β-carboline, melting point 179° C.

6-benzyloxy-4-methoxymethyl-3-(3-thienyl)-β-carboline, melting point 211°–213° C.

6-benzyloxy-4-methoxymethyl-3-(3-pyridyl)-β-carboline, melting point 195°–196° C.

6-benzyloxy-4-methoxymethyl-3-(2-benzothienyl)-β-carboline, melting point 224°–226° C.

6-benzyloxy-4-methoxymethyl-3-(2-methoxyphenyl)-β-carboline, melting point 202°–20° C.

EXAMPLE 2

6-Benzyloxy-4-methoxymethyl-3-(2-methyl-4-thiazolyl)-β-carboline a.)

0.530 g of 6-benzyloxy-3-bromoacetyl-4-methoxymethyl-9-tosyl-β-carboline is refluxed for 3 hours in 50 ml of ethanol with 0.07 g of thioacetamide. After concentration by evaporation the residue is chromatographed on silica gel with cyclohexane and ethyl acetate=1+1 as eluant. 0,260 g of 6-benzyloxy-4-methoxymethyl- 3-(2-methyl-4-thiazolyl)-9-tosyl-β-carboline of a melting point 181°–182° C. is obtained.

In a analogous way, there is produced:

6-benzyloxy-4-methoxymethyl-3-(2-phenyl-4-thiazolyl)-9-tosyl-β-carboline, melting point 173°–175° C.

b.)

0.260 g of 6-benzyloxy-4-methoxy-3-(2-methyl-4-thiazolyl)-9-tosyl-β-carboline is refluxed for 3 hours in 30 ml of a sodium alcoholate solution (0.015 g of sodium in 30 ml of methanol). After concentration by evaporation the organic phase, it is chromatographed on silica gel with hexane+acetone=1300+700. 0.180 g of 6-benzyloxy-4-methoxymethyl-3-(2-methyl- 4-thiazolyl)-β-carboline of a melting point of 260° C. (decomposition) is obtained.

In a analogous way, there is produced:

6-benzyloxy-4-methoxymethyl-3-(2-phenyl-4-thiazolyl) -β-carboline, melting point 134°–135° C.

EXAMPLE 3

6-Benzyloxy-4-methoxymethyl-3-(5-oxazolyl)-carboline 1.04 g of 6-benzyloxy-4-methoxymethyl-β-carboline-3-carbaldehyde and 0.68 g of tosylmethylisocyanide are added to a suspension of 1 g of powdered potassium carbonate in 30 ml of methanol. The batch is stirred first for 2 hours at room temperature and then refluxed for 1 hour. After concentration by evaporation it is taken up in 100 ml of ethyl acetate and the organic phase is washed twice each with 50 ml of 1 m-sodium hydroxide solution, dried, filtered and concentrated by evaporation. The residue is absorptively precipitated with ether and 550 mg of 6-benzyloxy-4-methoxymethyl-3-(5-oxazolyl)-β-carboline of a melting point of 208°–210° C. is obtained.

EXAMPLE 4

5-Benzyloxy-4-methoxymethyl-3-(5-ethyl-1,3,4-oxadiazol-2-yl)-β-carboline 1.60Orthopropionic acid triethyl ester is added to a suspension of 0.3 g of 5-benzyloxy-4-methoxymethyl-β-carboline-3-carboxylic acid hydrazide in 20 ml of methanol and then refluxed for 4 hours. After the concentration by evaporation the residue is mixed in 20 ml of n-butanol with 0.14 g of potassium-tert.-burylate and refluxed for another 5 hours. After the distilling off of the solvent it is taken up in methylene chloride and washed once each with saturated sodium bicarbonate and common salt solution. The organic phase is dried, filtered and concentrated by evaporation. The residue is chromatographed on silica gel with methylene chloride: ethanol=1:1. 0.236 g of 5-benzyloxy-4-methoxymethyl-3-(5-ethyl-1,3,4-oxadiazol-2-yl)-β-carboline of a melting point of 230°≧233° C. is obtained.

In a analogous way, there are produced:

6-benzyloxy-4-methoxymethyl-3-(5-methyl-1,3,4-oxadiazol-2-yl)-β-carboline, melting point 234°–235° C.

6,7-dimethoxy-4-ethyl-3-(5-methyl-1,3,4-oxadiazol-2-yl)-β-carboline, melting point 265°–268° C.

6-benzyloxy-4-ethyl-3-(5-methyl-1,3,4-oxadiazol-2-yl)-β-carboline, melting point 259°–260° C.

5-(4-chlorophenoxy)-4-methoxymethyl-3-(5-methyl-1,3,4-oxadiazol- 2-yl)-β-carboline, melting point 257°–259° C.

5-(4-chlorophenoxy)-4-methoxymethyl-3-(5n-butyl-1,3,4-oxadiazol- 2-yl)-β-carboline, melting point 215°–217° C.

6-benzyloxy-4-methoxymethyl-3-(5-methoxymethyl-1,3,4-oxadiazol- 2-yl)-β-carboline, melting point 180°–182° C.

5-(4-chlorophenoxy)-4-methoxymethyl-3-(5-methoxymethyl-1,3,4-oxadiazol- 2-yl)-β-carboline, melting point 216°–218° C.

6-benzyloxy-4-methoxymethyl-3-(5-cyclopropyl-1,3,4-oxadiazol- 2-yl)-β-carboline, melting point 235°–237° C.

5-isopropyloxy-4-methyl-3-(5-cyclopropyl-1,3,4-oxadiazol- 2-yl)-β-carboline, melting point 228°–232° C.

5-isopropyloxy-4-methyl-3-(5-methoxymethyl-1,3,4-oxadiazol-2-yl)-β-carboline, melting point 220°–222° C.

5-benzyloxy-4-methoxymethyl-3-(5-methoxymethyl-1,3,4-oxadiazol- 2-yl)-β-carboline, melting point 195°–198° C.

5-benzyloxy-4-methoxymethyl-3-(5-methyl-1,3,4-oxadiazol- 2-yl)-β-carboline, melting point 215°–216° C.

5-benzyloxy-4-methoxymethyl-3-(5-H-1,3,4-oxadiazol-2-yl)-β-carboline, melting point 200°–205° C.

6-benzyloxy-4-methoxymethyl-3-(5H-1,3,4-oxadiazol-2-yl)-β-carboline, melting point 233°–235° C.

5-(4-fluorobenzyloxy)-4-methoxymethyl-3-(5-ethyl-1,3,4-oxadiazol- 2-yl)-β-carboline, melting point 243°–244° C.

EXAMPLE 5

6-Benzyloxy-4-methoxymethyl-3-(5-amino-1,3,4-oxadiazol-2-yl)-β-carboline 0.376 g of 6-benzyloxy-4-methoxymethyl-β-carboline-3-carboxylic acid hydrazide is mixed in 10 ml of methanol with 0.106 g of bromocyanogen and heated for 1 hour to 40°–45° C. After cooling the reaction solution is made alkaline with ammonia solution and the precipitate is suctioned off, washed with water and dried. After absorptive precipitation with cyclohexane/ethyl acetate, 0.372 g of 6-benzyloxy-4-methoxymethyl-3-(5-amino-1,3,4-oxadiazol- 2-yl)-γ-carboline of a melting point of 290°–293° C. is obtained.

We claim:

1. A compound of formula I

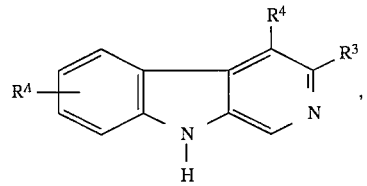

in which

R$^A$ means halogen, —CHR$^1$—R$^2$, phenyl optionally substituted with halogen, C$_{1-4}$-alkoxy or amino, hetary containing 5–6 ring atoms and 1–3 sulfur, oxygen and/or nitrogen heteroatoms or OR$^5$ optionally single to double substituted and R$^1$ represents hydrogen or C$_{1-4}$-alkyl, R$^2$ represented hydrogen, C$_{1-4}$-alkyl, —O—C$_{1-4}$-alkyl or an optionally substituted phenyl, benzyl or phenoxy radical and R$^5$ represents hydrogen, C$_{1-6}$-alkyl, C$_{3-7}$-cycloalkyl or an optionally substituted phenyl, benzyl, hetaryl containing 5–6 ring atoms and 1–3 sulfur, oxygen and/or nitrogen heteroatoms or benzocondensed hetaryl radical containing 5–6 ring atoms and 1–3 sulfur, oxygen and/or nitrogen heteroatoms, R$^4$ represents hydrogen, C$_{1-4}$-alkyl or C$_{1-4}$-alkoxy-C$_{1-2}$-alkyl and R$^3$ represents a monocyclic or bicyclic hetaryl radical containing 5–12 ring atoms and 1–3 sulfur, oxygen and/or nitrogen heteroatoms optionally substituted singly or multiply with C$_{1-4}$-alkyl, C$_{3-7}$-cycloalkyl, halogen, C$_{1-4}$-alkoxy-C$_{1-2}$-alkyl, phenyl or amino with the provision that R$^3$ is not substituted or unsubstituted 1,2,4-oxadiazolyl or isoxazolyl, as well as their steroisomers isomers and physiologically compatible acid addition salts.

2. 5-benzyloxy-4-methoxymethyl-3-(2-thienyl)-β-carboline 5-benzyloxy-4-methoxymethyl-3-(2-pyrrolyl)-β-carboline 6-benzyloxy-4-methoxymethyl-3-(2-methoxyphenyl)-β-carboline 6-benzyloxy-4-methoxymethyl-3-(2-methyl-4-thiazolyl)-β-carboline 6-benzyloxy-4-methoxymethyl-3-(5-oxazolyl)-β-carboline 5-benzyloxy-4-methoxymethyl-3-(5-ethyl-1,3,4-oxadiazol-2-yl)-β-carboline 6,7-dimethoxy-4-ethyl-3-(5-methyl-1,3,4-oxadiazol-2-yl)-β-carboline 5-(4-chlorophenoxy)-4-methoxymethyl-3-(5-methoxymethyl-1,3,4-oxadiazol-2-yl)-β-carboline 5-isopropyloxy-4-methyl-3-(5-cyclopropyl-1,3,4-oxadiazol-2-yl)-62 -carboline 5-(4-fluoro-benzyloxy)-4-methoxymethyl-3-(5-ethyl-1,3,4-oxadiazol-2-yl)-62 -carboline.

3. Process for the production of the compounds of formula I of claim 1 wherein a compound of formula II

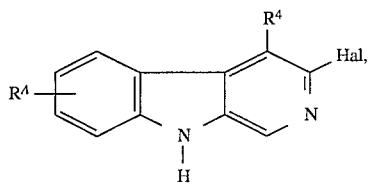

in which
- $R^A$ and $R^4$ have the above meaning and Hal is halogen, is arylated in the presence of a nickel or palladium catalyst with an organometallic compound of formula III $$R^3-Me-X_n \qquad \text{III,}$$

in which
- $R^3$ has the above meaning,
- Me means a metal atom,
- X means halogen, hydroxy or $C_{1-4}$-alkyl and
- n means 1 to 3, or b) a compound of formula IV

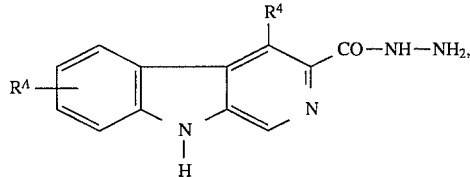

in which $R^A$ and $R^4$ have the above meaning, is cyclized with orthocarboxylic acid esters to compounds of formula I with $R^3$ meaning a 1,3,4-oxadiazol-2-yl radical, that is optionally substituted with $C_{1-4}$-alkyl, $C_{1-4}$-alkoxy-$C_{1-2}$-alkyl, phenyl or $C_{3-7}$-cycloalkyl or is cyclized with bromocyanogen to a compound of formula I with $R^3$ meaning a 5-amino-1,3,4-oxadiazol-2-yl radical or c) a compound of formula V

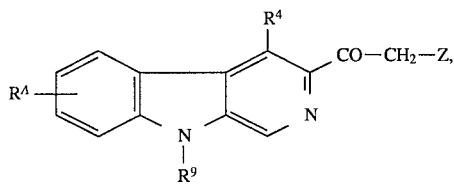

in which
- $R^A$ and $R^4$ have the above meaning, Z is halogen and $R^9$ represents hydrogen or a protective group, is cyclized with thiocarboxylic acid amides to compounds of formula I with $R^3$ meaning a thiazol-4-yl radical optionally substituted in 2-position and then the protective group is optionally cleaved off or d) a compound of formula VI

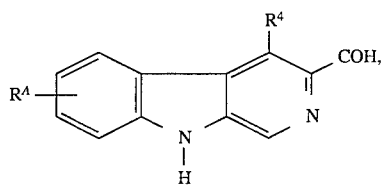

in which
- $R^A$ and $R^4$ have the above meaning is cyclized with tosylmethylisocyanide in the presence of bases to compounds of formula I with $R^3$ meaning an oxazol-5-yl radical and optionally then the benzyl group $R^5$ is cleaved off or $R^A$ meaning hydroxy is etherified or the isomers separated or the acid addition salts formed.

4. A compound of formula I

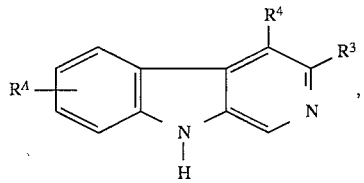

in which
- $R^A$ means halogen, —$CHR^1$—$R^2$, phenyl optionally substituted with halogen, $C_{1-4}$-alkoxy or amino, hetaryl containing 5–6 ring atoms and 1–3 sulfur, oxygen and/or nitrogen heteroatoms or $OR^5$ optionally single to double substituted and
- $R^1$ represented hydrogen or $C_{1-4}$-alkyl,
- $R^2$ represents hydrogen, $C_{1-4}$-alkyl, —O—$C_{1-4}$-alkyl or an optionally substituted phenyl, benzyl or phenoxy radical and
- $R^5$ represented hydrogen, $C_{1-6}$-alkyl, $C_{3-7}$-cycloalkyl or an optionally substituted phenyl, benzyl, hetaryl containing 5–6 ring atoms and 1–3 sulfur, oxygen and/or nitrogen heteroatoms or benzocondensed hetaryl radical containing 5–6 ring atoms and 1–3 sulfur, oxygen and/or nitrogen heteroatoms,
- $R^4$ represents hydrogen, $C_{1-4}$-alkyl or $C_{1-4}$-alkoxy-$C_{1-2}$-alkyl and
- $R^3$ represents thienyl, furyl, pyranyl, pyrrolyl, pyrazolyl, pyridyl, pyrimidinyl, pyridazinyl, oxazolyl, thiazolyl, isothiazolyl, 1,3,4-oxadiazol-2-yl, quinolyl, isoquinoly, benzothienyl or benzofuryl, as well as their stereoismers isomers and physiologically compatible acid addition salts.

* * * * *